United States Patent [19]

Grenner

[11] Patent Number: 4,918,025
[45] Date of Patent: Apr. 17, 1990

[54] SELF CONTAINED IMMUNOASSAY ELEMENT

[75] Inventor: Gerd Grenner, Lincoln, Mass.

[73] Assignee: PB Diagnostic Systems, Inc., Westwood, Mass.

[21] Appl. No.: 21,136

[22] Filed: Mar. 3, 1987

[51] Int. Cl.[4] .................... C12Q 1/00; G01N 31/22
[52] U.S. Cl. ........................... 436/165; 422/56; 422/58; 422/101; 422/82.05; 422/82.08; 422/82.09; 422/102; 435/4; 435/7; 436/807
[58] Field of Search ............... 422/56, 58, 102, 68, 422/101; 436/807, 165; 435/4, 7

[56] References Cited

U.S. PATENT DOCUMENTS

| | | | |
|---|---|---|---|
| 3,799,742 | 3/1974 | Coleman et al. | 422/102 X |
| 4,116,638 | 9/1978 | Kenoff | 422/99 |
| 4,168,146 | 9/1979 | Grubb et al. | 435/7 X |
| 4,426,451 | 1/1984 | Columbus | 436/518 |
| 4,447,546 | 5/1984 | Hirschfeld | 436/527 |
| 4,472,353 | 9/1984 | Moore | 422/56 |
| 4,690,899 | 9/1987 | Klose et al. | 422/102 X |
| 4,690,907 | 9/1987 | Hibino | 436/514 |
| 4,708,931 | 11/1987 | Christian | 436/807 X |
| 4,717,656 | 1/1988 | Swanljung | 422/58 X |
| 4,740,475 | 4/1988 | Paul | 422/58 X |
| 4,806,316 | 2/1989 | Johnson et al. | 422/58 X |
| 4,849,340 | 7/1989 | Oberhardt | 436/526 X |

FOREIGN PATENT DOCUMENTS

| | | |
|---|---|---|
| 0073513 | 3/1983 | European Pat. Off. . |
| 0142914 | 5/1985 | European Pat. Off. . |
| 0167171 | 1/1986 | European Pat. Off. . |
| 0186100 | 7/1986 | European Pat. Off. . |
| 7602181 | 8/1976 | France . |
| 7712933 | 11/1978 | France . |
| 8202211 | 7/1982 | Int'l Pat. Institute . |
| 8603589 | 6/1986 | Int'l Pat. Institute . |
| WO82/02601 | 8/1982 | PCT Int'l Appl. . |
| WO86/06488 | 11/1986 | PCT Int'l Appl. . |

*Primary Examiner*—Christine M. Nucker
*Assistant Examiner*—Jill Johnston
*Attorney, Agent, or Firm*—Gaetano D. Maccarone

[57] ABSTRACT

An element for analysis of a liquid sample including a capillary containing a fixed reagent in fluid communication with reagent reservoirs and a waste liquid reservoir. A sample introducing means is provided which permits analyte in a sample to interact with the fixed reagent. A labelled reagent is provided which interacts with either the fixed reagent or the analyte in a manner which permits detection of the concentration of analyte in the sample. The capillary, reagent reservoirs, waste liquid reservoir and the sample introducing means are arranged within a common housing so that reagent waste liquid need not be removed from the element.

24 Claims, 3 Drawing Sheets

SELF CONTAINED IMMUNOASSAY ELEMENT

BACKGROUND OF THE INVENTION

The present invention relates to a capillary device for conducting immunoassay tests. More particularly, the present invention relates to a capillary device for conducting an immunoassay test which device contains the reagents necessary for carrying out the test and confines the reagents and sample tested within the device during the course of the test.

Immunoassay tests are used for the detection in body fluids of a wide variety of compositions including antigens, antibodies, infectious agents and hormones. The purpose of the immunoassay test is to measure the degree of interaction between an antigen and its corresponding antibody.

It has been proposed to utilize various wet chemistry processes wherein the immunoassay interactions are conducted in tubes or plates containing multiple compartments wherein an antibody or an antigen is coated in the surface of the tube or compartment. The use of these devices requires a number of steps of applying and then removing reagents from the compartments or tubes and requires that the volume of these reagents be accurately measured. In addition, relatively large samples are required to conduct the immunoassay test in these devices. An additional serious problem associated with these wet chemistry techniques is the disposal of biological liquids which may contain infectious agents.

European Patent Application 0,142,914 discloses a self-contained microassay card which houses a wash liquid, a plurality of separated reagents and a microassay rod upon which the assay is effected. The use of the card requires the use of a syringe in order to introduce a precise volume of the sample into the chamber housing the microassay rod. This requires a separate step of measuring the precise volume desired. In addition, since the syringe is required to deliver the sample under pressure, the chamber housing the microassay rod must be closed to avoid loss of sample which in turn requires a precision fit plug. Since no provision is made in the device for a filter means, whole blood cannot be processed thereby requiring an additional step for separating the cellular components from the plasma components prior to initiating the microassay. Lastly, the device requires the precise positioning of pressure means at various locations on the outside surface of the device in order to effect proper sequencing of reagents to contact sample components during the test. The requirement of precise positioning at the proper time during the test introduces a major source of error for the test.

European Patent Application 0 073,513 discloses a device for conducting assays which includes a rotor upon which are positioned a plurality of elements which house reagents in separate compartments. The compartments are located within an element at different radial positions on the rotor and at least one compartment is in fluid communication with a sample application chamber located at the radially innermost position of the compartment. A mixing chamber which allows for the introduction of a liquid reagent is located within a compartment at a radially intermediate position and a measurement chamber is located at the radially outermost position of the compartment. Liquid sample and/or liquid reagent are moved from compartment to compartment and eventually to the measurement chamber by means of conduits connecting the compartments and centrifugal force caused by rotating the rotor. This mode of operation requires that the conduits be of precise size and that the rates of rotation be precisely controlled otherwise liquid flow into the wrong compartments occurs. These requirements introduce a serious source of error in the assay.

P.C.T. publication number W082/02601 discloses a solid phase assay system which utilizes a porous solid matrix such as treated paper or a mat of fibers. A binding material is reacted with its antibody within the solid matrix to immobilize the reaction product within the matrix. The amount of binding material and its antibody that are reacted must be very accurately controlled using accurate volumetric micropipettes. Solutions of analyte and labelled indicator then are applied to the matrix to effect the assay either as a competitive assay or as a sandwich assay. Unbound labelled indicator is removed from the matrix by a chromatographic procedure utilizing a solvent. The concentration of labelled indicator in the reaction zone then is measured. This assay is undesirable since it requires measuring precise volumes, manual washing steps and the pipetting of reagents. It is also unsuitable for assaying whole blood.

European Patent Application 0 186 100 discloses a solid phase assay which utilizes a fiber matrix coated with a polymer capable of retaining a reagent which binds with an analyte of interest. A second reagent is bound to the bound analyte and a third reagent is introduced which, in the presence of the second reagent, produces a detectable response. The disadvantage of this assay is that it requires precise volumes of reagent and sample which requires time-consuming volume measurement steps.

U.S. Pat. No. 4,426,451 discloses a device for conducting an assay which utilizes two continuous capillary zones in fluid communication with each other. A narrow passageway is provided between the two zones in order to temporarily stop liquid flow between the zones. Liquid transfer between the zones is initiated by a pulse or pressure and completed by capillary action to the zone having the smaller capillary. The device is useful for conducting competitive assays or for separating whole blood into a cellular component and a plasma component. Since no means are provided for at least one washing step and since separation of bound species from unbound species relies solely upon capillary action, incomplete separation of bound from unbound species occurs. This leads to error in the assay. In addition, the device does not permit conducting a sandwich assay.

It has been proposed in French Patent Application Number 7712933, published Nov. 24, 1978 to conduct immunoassays in a capillary tube. However, no means are provided for filling the capillary and for eliminating the need for removing reagents and reaction products from the capillary. Thus, the problem of disposing infectious materials is still present.

P.C.T. publication number W086/06488 discloses a test apparatus for performing chemical, clinical diagnostic and like tests. The apparatus includes a housing, a sample receiving area and a plurality of rupturable containers in recesses within the housing. The containers include the predetermined amount of one of the specific reagents which are required for the test. A duct or channel connects each area with the sample receiving area where the sample is located. A member is provided in association with each container to enable the container to be ruptured when addition of the specific reagent is required in the test. This assay apparatus does not include a self-metering sample application element. Instead it requires an operator to pipette a precisely measured volume of the sample onto the sample receiving membrane. The membrane thickness is not precisely defined and therefore the apparatus is not capable of providing very accurate quantitative results. Further, the fluid stream in the apparatus is not very well defined with the result that very high volumes of wash liquid, e.g., about 1-2 ml, must be used because the liquid must cover the entire test element.

It would be highly desirable to provide a means for conducting immunoassay tests under conditions which require only small samples, which provide accurate test results, which eliminates the need for measuring precise volumes of reagents, which permits the testing of whole blood and which eliminates the problems associated with disposing of infectious liquids.

SUMMARY OF THE INVENTION

The present invention provides a self-contained immunoassay element which comprises a housing which includes one or more reservoirs containing a reagent or a wash solution used in the assay, means for introducing a sample into the element and a capillary tube in fluid communication with the means for introducing the sample as well as with the reagent and wash solution reservoirs. At least a portion of a surface of the capillary tube, which is the reaction zone of the element, is coated with an antigen or an antibody which is interactive with the analyte contained within the liquid sample for which the analysis is being conducted. A reservoir which is in fluid communication with the capillary is provided for spent reagent and spent wash solution. The element is constructed so that, except for introducing the sample from an outside source into the element, all interactions among reagents used in the assay and all wash steps are conducted within the element and waste liquids resulting from the assay are retained within the element. Each reagent and/or wash solution is contained within a separate reservoir and is provided with means for passing the reagent or wash solution under pressure into the capillary.

In operation, a liquid sample containing an analyte is introduced into the element and at least a portion of the sample enters the capillary under the force of capillary action and is retained therein for a sufficient time period to allow the analyte to interact with the bound first reagent (antigen or antibody) in the capillary to form a first nondiffusible species. A labelled reagent positioned either in a reservoir or in the means for introducing the sample within the element is introduced into the capillary either simultaneously with the analyte or subsequently to introducing the analyte into the capillary. Since the capillary is filled with liquid by means of capillary action, the volume of liquid containing the analyte or a reagent in the capillary taking part in the assay is always accurately controlled. After the desired interactions between the first reagent, the labelled reagent and the analyte have been completed excess labelled reagent is removed by washing. The wash solution is contained in a reservoir within the element and is passed under pressure from the reservoir into the capillary. The wash solution thus carries the noninteracted reagent(s) into a waste reservoir located within the element. The label portion of the labelled reagent is detected to provide the concentration of the analyte present in the sample. Depending upon the type of label which is utilized, it may be detected directly or it may be detected indirectly such as by interaction with yet another reagent which is brought into the capillary from a reservoir located in the element. Any liquid in the capillary which is replaced by the latter reagent will be passed into the waste reservoir.

This invention provides a number of significant advantages over the prior art immunoassay elements. Since the interaction of the reagent(s) and the analyte is conducted in a very thin, flat capillary tube the fluid stream is very well defined. Therefore, only small volumes of sample and reagents are utilized. Since those volumes are fixed by the volume of the capillary, no volume measurements are required. Whole blood can be utilized as a sample by incorporating appropriate filtration means which separates whole blood into a cellular component and a plasma component in the means for introducing the sample into the element. The sample need not be diluted thereby eliminating prior art dilution steps which require volume measurements. Since the capillary volume is small, liquid can be introduced therein without additional means other than capillary action and can be removed therefrom easily by virtue of the small volume by washing. In addition, since the reagents and waste liquid are retained within the self-contained element, the dangers associated with disposing of a potentially infectious liquid are eliminated. The entire element can be disposed of safely such as by burning without contact with the liquids within the element.

DESCRIPTION OF SPECIFIC EMBODIMENTS

Figure 1:
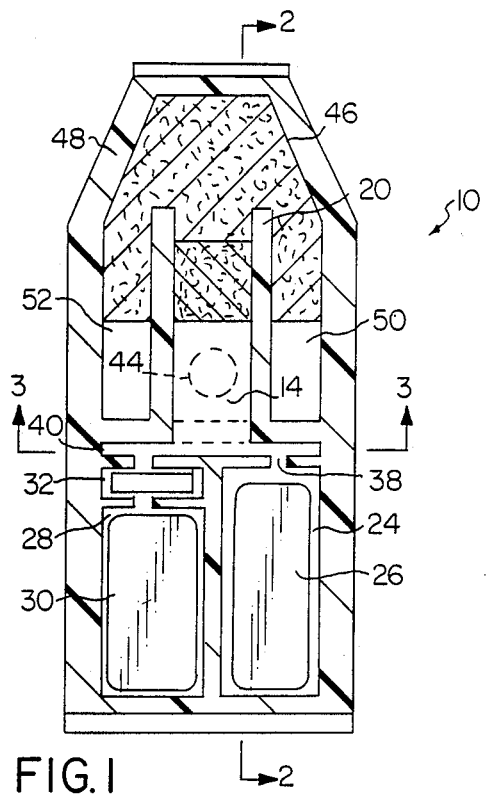
FIG. 1 is a top view of an element of this invention.
Figure 3:
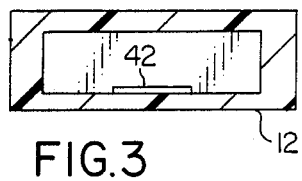
FIG. 3 is a cross-sectional view taken along line 3—3 of FIG. 1.
Figure 2:
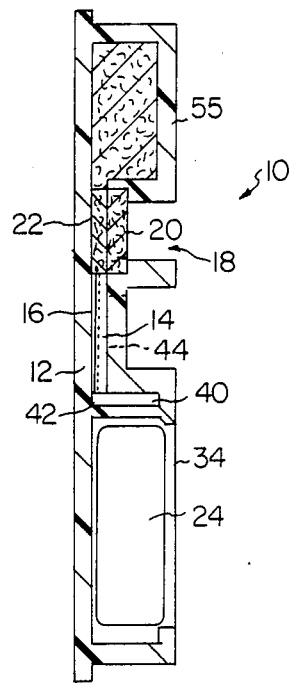
FIG. 2 is a cross-sectional side view taken along line 2—2 of FIG. 1.

Referring to FIGS. 1-3, the analytical element of this invention 10 is formed so that a top section and a bottom section are joined together to form a housing which includes a capillary tube, a sample introducing means, at least one reservoir for a reagent and/or wash solution, and a waste reservoir wherein the capillary, each reservoir and the sample introducing means are in fluid communication with each other. The element 10 typically has a width of from about 10 to about 20 mm, preferably about 15 mm, an overall length of from about 30 mm to about 50 mm, preferably about 40 mm, and a height of from about 3 to about 8 mm, preferably about 5 mm. The bottom section can comprise a plate 12 which is adhered to the top section comprising a plurality of walls and reservoirs as shown generally in FIGS. 1 and 2. A capillary tube 14 is provided in a central portion of the element 10 and the capillary tube 14 includes at least one surface, here shown as the bottom surface 16 of the tube, which has bonded to at least a portion thereof a first reagent which is capable of interacting, either directly or indirectly, with the analyte of interest present in the sample. Thus, the surface of the capillary tube which has the first reagent bonded thereto defines the reaction zone of the element. The capillary tube 14 is typically from about 0.02 mm to about 0.5 mm, and preferably from about 0.05 mm to about 0.2 mm, in height; from about 1 to about 10 mm, and preferably from about 3 to about 5 mm, in width; and from about 5 to about 25 mm, and preferably from about 8 to about 12 mm, in length. The surfaces of the capillary tube 14 may be smooth or roughened, e.g., grooved. In the latter instances a large amount of the first reagent may be bonded to a give unit area of the surface.

An opening 18 is provided in the housing to permit the sample to be introduced into the element 10. The sample volumes typically required for use with the immunoassay element range from about 20 to about 100 ul, preferably from about 30 to about 50 ul. As shown in FIGS. 1–3, the sample introduction means includes an optional filter 20 and a membrane layer 22. The filter may be provided in embodiments where it is desired to use whole blood samples for example, to remove components therefrom. The filter element 20 may be any suitable material, synthetic or naturally occurring, or a mixture of each type, which is capable of removing from the fluid sample any component(s) which could interfere with the analysis and which is inert to the analyte(s) of interest, that is, will not prevent any significant amount of said analyte(s) from passing through the filter whether because of adsorption, reaction or otherwise. The type of filter material utilized in any instance is dependent upon the type of biological fluid to be analyzed. For, example, a microporous filter element may be used to remove bacteria cells or microorganisms from the sample fluid. In a preferred embodiment where the sample is whole blood, the filter element comprises a fibrous material which is capable of separating cells, e.g., erythrocytes, leucocytes, etc., from plasma or serum. Typical suitable fibrous materials include glass, quartz, cellulose acetate, cellulose, synthetic polymeric fibers such as polyamides or polyesters, and the like. The fibrous material may be treated with a material such as gelatin, either inert or deionized, or serum albumin to substantially reduce or eliminate any binding thereto by an analyte of interest. Further, the filter element 20 may be impregnated with a material which is capable of removing specific components from the fluid sample, for example, lipoproteins. Titanium dioxide is suitable for this purpose. The membrane 22 may contain a labelled reagent which is interactive with either the analyte of interest or the first reagent which is fixed to the surface of the capillary.

A first reservoir 24 is provided which contains a wash solution. The wash liquid may be simply sealed in the reservoir or it may be provided in a pod 26 as illustrated. A second reservoir 28 may also be provided, when necessary, for a reagent which is capable of interacting with the label moiety of the labelled reagent in order to render the label detectable as where the label is an enzyme and the reagent is a substrate for the enzyme. As illustrated the reagent is provided in a pod 30. In one embodiment, the reagent which is adapted to render the label detectable can be provided in a separate reservoir 32 in a paper matrix, membrane matrix or the like. Pod 26, as shown, is enclosed within reservoir 24 by means of a thin layer 34 of a flexible material such as aluminum foil or the like which seals the reservoir 24 from the atmosphere. By exerting pressure on the thin layer 34 such as with a plunger (not shown) and consequently applying pressure on pod 26, the pod can be burst and the liquid therein caused to enter the capillary tube 14 by passing through opening 38, passageway 40 and opening 42. In like manner, the liquid in pod 30, when present, can be caused to enter the capillary tube 14. A transparent zone, or window, 44 is provided in the housing above at least the reaction zone of the capillary tube in order to permit readout of the reaction zone by a conventional detection device such as a densitometer, fluorimeter or the like.

A waste reservoir 46 is provided to receive waste sample, wash reagent or waste wash solution from the capillary tube. The waste reservoir 46 may include a liquid absorbent 48 and open areas 50 and 52 in order to provide sufficient volume capacity to retain all the waste sample, reagent, etc., utilized in the assay. Also, there may be provided an air hole in the top surface 55 of waste reservoir 46 to allow the waste liquids to fill the reservoir. In the embodiment illustrated in FIGS. 1–3 the wate liquids pass from the capillary tube 14 through membrane 22 and into waste reservoir 46.

The immunoassay elements of the invention may be fabricated by initially making two separate parts, i.e., an upper part and a lower part. The bottom part would include the bottom surface of the capillary tube and the walls and bottom surface of the reservoirs. After binding the first reagent to the capillary tube surface and depositing the wash solution and, where necessary the additional reagent, in the appropriate reservoirs, the upper and lower parts are brought together and sealed such as by ultrasonic welding, heat and pressure, etc. The housing of the element may be made from any suitable material including, for example, synthetic polymeric materials which are easily moldable. A preferred material is polystyrene which has been treated with gamma radiation to enhance its ability to bind antigens or antibodies. The housing may be transparent or opaque, provided that where it is opaque there is a transparent window to allow detection of the labelled species which is obtained as a result of the interaction between the analyte and reagents.

Figure 4:
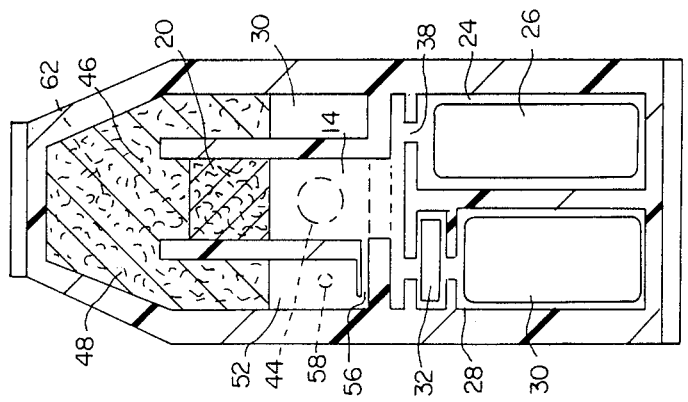
FIG. 4 is a view of an alternative element of this invention.

FIG. 4, wherein the referenced elements having the same numerical reference as those shown in FIGS. 1 through 3 are the same elements, illustrates another embodiment of the invention. In this embodiment the capillary tube 14 is modified to include a second capillary outlet 56, which permits air passage therethrough, and there is also provided a hole 58 in the upper surface of the waste reservoir in the vicinity of outlet 56 to assure that the capillary tube 14 becomes filled with liquid. The element may also include an air hole 62 in the upper surface of the waste reservoir as shown in FIGS. 1–3. The air holes 58 and 62 may be made suitably small, or they may be covered with a hydrophobic material such as a hydrophobic porous membrane, to allow passage of air while preventing passage of liquid.

Figure 5:
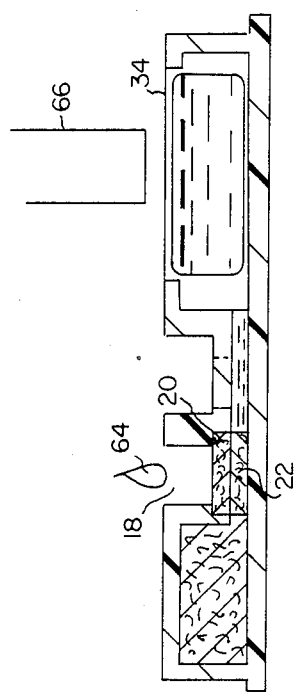
FIGS. 5 and 6 are cross-sectional views of the element of this invention illustrating its mode of operation.
Figure 6:
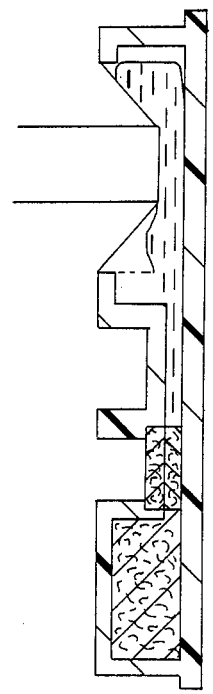

FIGS. 5 and 6 illustrate an embodiment of the immunoassay element wherein there is provided one reagent reservoir containing a volume of reagent sufficient to function both as a wash liquid and as a reagent for interacting with the reagent bound to the capillary and/or the analyte to render the label detectable. In operation a drop of whole blood 64 is introduced through opening 18 onto filter 20 which separates the blood cells from the blood plasma. The plasma passes into membrane 22 which includes a labelled reagent which interacts with at least part the sample analyte to form a conjugate. The plasma, together with the conjugate migrates into capillary tube 14 by means of capillary action. After the capillary has been filled and the plasma is allowed to incubate within the capillary for the required period of time during which the interactions between the sample analyte, labelled reagent and the reagent bound to the surface of the capillary tube go to completion, plunger 66 is pushed downwardly so as to contact foil layer 34 and exert sufficient pressure on pod 26 to cause the pod to be ruptured. The reagent is carried into the capillary tube 14 and at the same time it displaces the plasma containing any unbound analyte, labelled reagent or conjugate suspended or dissolved therein. The displaced plasma passes into waste reservoir 46 containing absorbent material 48. During the preceding incubation period, substantially all of the analyte will have interacted with the labelled reagent and the reagent bound to the surface of the capillary tube. By virtue of these interactions the bound species which is formed will remain in the capillary and is not displaced by the incoming reagent. After a suitable incubation period to allow the reagent to render the label detectable, it is detected through transparent window 44 by means of an appropriate conventional detection apparatus.

Figure 7:
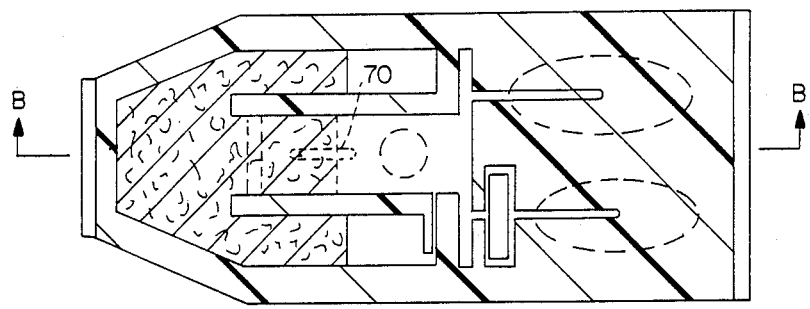
FIG. 7 is a top view of an alternative element of this invention.
Figure 8:
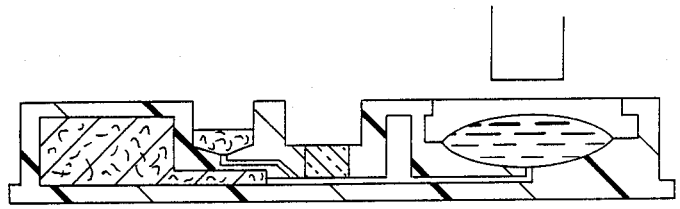
FIG. 8 is a cross-sectional side view taken along line 8—8 of FIG. 7.

FIGS. 7 and 8 illustrate an immunoassay element according to the invention where the wash liquid and/or reagent reservoirs are filled with the liquid(s) and pods are not utilized. As pointed out previously such reservoirs can be formed in two parts which are then brought together, capillary tube 14 by means of capillary action. The element includes a filling capillary 70 which allows the fluid which passes through membrane 22 to enter capillary tube 14 by capillary action. In this embodiment, fluid which is initially present in capillary tube 14 and then expelled therefrom by wash solution and/or a reagent passes into waste reservoir without having to pass through membrane 22. The other elements of the device and the operation thereof are as described previously.

The immunoassay element of the invention may be used to carry out any of the known immunometric, sandwich or competitive assays for an analyte, e.g., an antigen or an antibody. These assays are well known to those skilled in the art and extensive discussion thereof is not required here. Briefly, in one type of sandwich assay wherein the assay element includes two reservoirs for reagent and/or wash fluid, a sample is applied to the sample inlet, migrates through a layer containing a labelled reagent thereby imbibing labelled reagent and passes into the capillary by virtue of capillary action. During a suitable incubation period the analyte in the sample interacts with the labelled reagent and with the reagent bound to a surface of the capillary. Subsequently, wash liquid is introduced from a reservoir within the element and passes into the capillary to displace the fluid present therein together with any uninteracted labelled reagent. The displaced fluid is forced into the waste reservoir. Another reagent, which is adapted to render the label moiety of the labelled reagent detectable, is introduced into the capillary and displaces the wash liquid which is forced into the waste reservoir. After a suitable incubation period the detectable signal formed in the capillary tube is measured.

In a second embodiment wherein a sandwich assay is conducted, three reservoirs containing wash solution and/or reagent are employed in the element. In the first step, a sample containing the analyte is introduced into the element and passes by capillary action into the capillary wherein the analyte interacts with the fixed first reagent in the capillary. In a second step, a labelled reagent which interacts with the analyte from a reservoir of the element is introduced into the capillary. In a third step, a wash solution from a reservoir of the element is introduced into the capillary to replace the liquid therein and cause the uninteracted liquid to pass into the waste reservoir. In a fourth step, a liquid containing a substrate which interacts with the label of the labelled reagent to render the label detectable is passed from a third reservoir into the capillary to replace the wash liquid therein and to cause the substrate to interact with the label fixed to the first reagent. The label rendered detectable then is observed through a transparent opening in the capillary.

As an example of the competitive assay, the sample containing an analyte is introduced into the element and mixed with a labelled analyte located within a porous layer within the sample introduction means. The sample, analyte and the labelled analyte then are introduced into the capillary by means of capillary action wherein they are interacted with a fixed first reagent which interacts with the analyte or labelled analyte. Thereafter, the noninteracted species is removed from the capillary by means of sufficient reagent which interacts with the label to form a detectable moiety. In this embodiment, only one reagent reservoir is required. In an alternative embodiment, the capillary is first washed with a wash liquid from one reservoir and then with a reagent which interacts with the label to form a detectable moiety in a second step. In this latter embodiment, two reservoirs are required.

Any chemical interaction which effects a change in the radiation emission in either the label of the labelled reagent or a reagent which interacts with the label to cause a change in radiation emission to provide a detectable signal can be exploited in accordance with the element of the invention. For example, any change in fluorescence, chemiluminescence, color or other change in visible or near visible radiation can be exploited. Thus, the label utilized in the labelled reagent may be directly or indirectly detectable. The label may be a fluorophore, chromophore, chemiluminophore, a phosphor or an enzyme. Where the label is an enzyme it can be one which interacts with a substrate to cause a change in absorption where the substrate is chromogen, in fluorescence if the substrate is a fluorophore, in chemiluminescence if the substrate is a chemiluminescent precursor or in phosphorescence where the substrate is a phosphor.

Although the invention has been described with respect to various embodiments thereof, it is not intended to be limited thereto but rather those skilled in the art will recognize that variations and modifications may be made therein which are within the spirit of the invention and the scope of the appended claims.

What is claimed is:

1. A self-contained element for analysis of a liquid sample containing a component to be determined which comprises:

a housing containing a capillary tube having opposed interior top and bottom surfaces, a portion of at least one of said top and bottom surfaces having bound thereto a first reagent consisting of either said component to be determined or the binding partner of said component to be determined, said bound first reagent defining a reaction zone and interactive with said component to be determined to form a first nondiffusible species, and at least one of said top and bottom surfaces including a transparent area to permit measurement of radiation from at least a portion of said reaction zone;

a labelled second reagent, said second reagent consisting of said component to be determined or the binding partner of said component to be determined and being interactive with said first nondiffusible species or said first reagent to form a second labelled species;

means for introducing at least a portion of said sample and said labelled second reagent into said capillary tube by capillary forces;

at least one reactant reservoir containing a wash solution or a third reagent which is interactive with said second labelled species, said at least one reactant reservoir being in fluid communication with said capillary tube;

a waste reservoir in fluid communication with said capillary tube adapted to receive waste fluid from said capillary tube;

and said means for introducing said sample and said labelled second reagent, said at least one reactant reservoir and said waste reservoir being housed within said housing.

2. The element of claim 1 wherein said means for introducing said sample into said capillary comprises an inlet and a porous membrane in fluid communication with said capillary.

3. The element of claim 2 including a filter element contiguous with said membrane.

4. The element of claim 1 wherein said means for introducing said sample includes said labelled reagent adapted to be introduced into said capillary with said sample.

5. The element of claim 4 wherein said labelled reagent is a labelled antibody.

6. The element of claim 4 wherein the label of said labelled reagent is an enzyme.

7. The element of any one of claims 2 or 3 wherein said porous membrane contains said labelled reagent adapted to be introduced into said capillary with said sample.

8. The element of any one of claims 2 or 3 wherein said porous membrane contains a labelled antibody.

9. The element of any one of claims 2 or 3 wherein the label of said labelled reagent is an enzyme.

10. The element of any one of claims 1, 2, 3 or 4 having one reactant reservoir.

11. The element of any one of claims 1, 2, 3 or 4 having two reactant reservoirs.

12. The element of any one of claims 1, 2, 3, or 4 having three reactant reservoirs.

13. The element of any one of claims 1, 2, 3 or 4 wherein said waste reservoir contains a liquid absorbing material.

14. A process for analyzing for an analyte in a liquid sample within the confines of a self-contained element housing which comprises:

introducing a liquid sample into a porous layer within said element, said porous layer containing a labelled reagent which is interactive with said analyte;

passing said analyte and said labelled reagent by capillary force into a capillary having opposed top and bottom surfaces and a first reagent bound to at least one of said top and bottom surfaces, said first reagent being interactive with said analyte and said labelled reagent to form a first nondiffusible species comprising said labelled reagent, said analyte and said first reagent;

washing the interior of said capillary with a liquid composition positioned in a reservoir within said element and in fluid communication with said capillary to pass the portion of the sample noninteracted with said first reagent into a wastereservoir located within said element, and rendering said labelled reagent detectable.

15. The process of claim 14 wherein said labelled reagent is rendered detectable after said analyte interacts with said first reagent and said labelled reagent.

16. The process of claim 14 wherein said labelled reagent is rendered detectable by washing said capillary with a sufficient amount of a liquid composition to remove noninteracted sample from said capillary and to form a detectable species with substantially all of the labelled reagent interacted with said analyte in said capillary.

17. The process of claim 14 wherein said labelled reagent is rendered detectable by washing said capillary with a wash solution to remove noninteracted sample from said capillary and replacing said wash solution in said capillary with a second liquid reagent.

18. The process of any one of claims 14, 15, 16 or 17 wherein said labelled reagent is labelled with an enzyme.

19. A process for analyzing for an analyte in a liquid sample within the confines of a self-contained element housing which comprises:

introducing by capillary forces a liquid sample into a capillary having opposed top and bottom surfaces and a first reagent bound to at least one of said surfaces, said first reagent being interactive with said analyte to form a first nondiffusible species comprising said analyte and said first reagent;

washing said capillary with a liquid wash composition positioned in a reservoir within said element, said reservoir being in fluid communication with said capillary to pass the portion of the sample noninteracted with said first reagent into a waste reservoir located within said element;

passing a labelled reagent interactive with said analyte from a reservoir within said element into said capillary and directing the liquid wash composition from said capillary into said waste reservoir;

incubating said labelled reagent and said first nondiffusible species to effect interaction between said analyte and said first reagent to form a second nondiffusible species;

and rendering said second nondiffusible species detectable.

20. The process of claim 19 wherein said labelled reagent is rendered detectable by washing said capillary with a sufficient amount of a liquid composition to remove noninteracted sample from said capillary and to form a detectable species with substantially all of the labelled reagent interacted with said analyte in said capillary.

21. A process for analyzing for an analyte in a liquid sample within the confines of a self-contained element housing which comprises:

introducing a liquid sample containing an analyte into a porous layer within said element, said porous layer containing a labelled reagent;

introducing by capillary forces the labelled reagent and said analyte into a capillary having an inner surface and a first reagent bound to said inner surface, said first reagent being interactive with said analyte to form a first nondiffusible species comprising said analyte and said first reagent and a second nondiffusible species comprising said first reagent and said labelled reagent;

washing said capillary with a liquid composition positioned in a reservoir within said element and in fluid communication with said capillary to pass the portion of the sample and labelled reagent noninteracted with said first reagent into a waste reservoir located with in said element and rendering said labelled reagent detectable.

22. The process of claim 21 wherein said labelled reagent is rendered detectable after said labelled reagent interacts with said first reagent.

23. The process of claim 21 wherein said labelled reagent is rendered detectable by washing said capillary with a sufficient amount of liquid composition to remove noninteracted sample from said capillary and to form a detectable species with substantially all of the labelled reagent interacted with said first reagent in said capillary.

24. The process of claim 21 wherein said labelled reagent is rendered detectable by washing said capillary with a wash solution to remove noninteracted sample from said capillary and replacing said wash solution in said capillary with a second liquid reagent.

* * * * *